United States Patent
Nishimura et al.

(10) Patent No.: US 10,591,498 B2
(45) Date of Patent: Mar. 17, 2020

(54) AUTOMATED ANALYSIS DEVICE (71) Applicant: Hitachi High-Technologies Corporation, Tokyo (JP)

(72) Inventors: Koichi Nishimura, Tokyo (JP); Hiroyuki Takayama, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 225 days.

(21) Appl. No.: 15/554,086

(22) PCT Filed: Feb. 1, 2016

(86) PCT No.: PCT/JP2016/052848
§ 371 (c)(1),
(2) Date: Aug. 28, 2017

(87) PCT Pub. No.: WO2016/139997
PCT Pub. Date: Sep. 9, 2016

(65) Prior Publication Data
US 2018/0038879 A1 Feb. 8, 2018

(30) Foreign Application Priority Data
Mar. 2, 2015 (JP) ................. 2015-039787

(51) Int. Cl.
*G01N 35/00* (2006.01)
*G01N 35/10* (2006.01)
(Continued)

(52) U.S. Cl.
CPC ....... *G01N 35/00623* (2013.01); *G01N 33/50* (2013.01); *G01N 35/00712* (2013.01);
(Continued)

(58) Field of Classification Search
CPC ............... G01N 35/1079; G01N 33/50; G01N 35/00623; G01N 35/10; G01N 35/00722;
(Continued)

(56) References Cited

U.S. PATENT DOCUMENTS

2002/0049650 A1* 4/2002 Reff ................... G06Q 10/0875
705/29
2006/0177344 A1* 8/2006 Ouchi ................ G01N 35/1002
422/64
(Continued)

FOREIGN PATENT DOCUMENTS

JP   2008-051543 A   3/2008
JP   2011-117814 A   6/2011
(Continued)

OTHER PUBLICATIONS

International Search Report of PCT/JP2016/052848 dated Apr. 26, 2016.

*Primary Examiner* — Mischita L Henson
(74) *Attorney, Agent, or Firm* — Mattingly & Malur, PC (57) ABSTRACT

Provided is an automatic analyzer capable of replacing an insertion mechanism while suppressing occurrence of dispensing abnormality and analysis result abnormality accompanying deterioration of the insertion mechanism. Included are an insertion mechanism that is inserted into a closed container through a lid of the container; a storage unit that stores an insertion history count corresponding to a cumulative load of the insertion mechanism caused by inserting the insertion mechanism into a plurality of the containers, and an allowable insertion history count which is an allowable value of the insertion history count; and a control unit that compares the insertion history count with the allowable insertion history count and performs control to make a notification to an operator in a case where the insertion history count reaches the allowable insertion history count.

11 Claims, 7 Drawing Sheets

(51) Int. Cl.
*G01N 35/02* (2006.01)
*G01N 33/50* (2006.01)

(52) U.S. Cl.
CPC ....... *G01N 35/00722* (2013.01); *G01N 35/02* (2013.01); *G01N 35/10* (2013.01); *G01N 35/1079* (2013.01); *B01L 2200/141* (2013.01); *G01N 35/1002* (2013.01); *G01N 2035/009* (2013.01)

(58) Field of Classification Search
CPC ......... G01N 35/1002; G01N 2035/009; G01N 35/02; G01N 35/00712; B01L 2200/141
See application file for complete search history.

(56) References Cited

U.S. PATENT DOCUMENTS

| | | |
|---|---|---|
| 2008/0050280 A1 | 2/2008 | Fujita |
| 2009/0281930 A1* | 11/2009 | Sakagami ........ G01N 35/00623 705/28 |
| 2014/0119994 A1 | 5/2014 | Ariyoshi et al. |

FOREIGN PATENT DOCUMENTS

| | | | | |
|---|---|---|---|---|
| JP | 2011117814 A | * | 6/2011 | ............ G01N 35/10 |
| JP | 2012-021871 A | | 2/2012 | |
| JP | 2014-089129 A | | 5/2014 | |
| JP | 6215018 B2 | * | 10/2017 | |
| WO | WO1998021595 A1 | * | 5/1998 | ............ G01N 35/02 |

* cited by examiner

AUTOMATED ANALYSIS DEVICE

TECHNICAL FIELD

The present invention relates to an automatic analyzer that performs qualitative and quantitative analysis of a biological sample such as blood or urine.

BACKGROUND ART

In an automatic analyzer, a predetermined process such as an analysis process is performed by dispensing a material contained in a sample container or a reagent container into a reaction container, a child specimen container, or the like. Usually, containers containing a material such as samples and reagents are hermetically sealed by a component such as a lid, and dispensing is performed by inserting a probe into a lid which is previously perforated, or by directly perforating the lid with a probe.

When repeatedly inserting a probe into a hermetically sealed container, even if the probe is inserted into a previously perforated lid, the probe comes into contact with the lid, such that there is a concern that a foreign matter may be generated due to the contact and may be mixed into the contained material. Therefore, the more repeatedly inserting it into the same lid, the higher the risk of contamination. Therefore, as the related art, for example, as in PTL 1, a technique in which the allowable insertion count N of the probe into the lid is set, and in a case where the number n of times of insertion exceeds the allowable insertion count, control is performed not to perform the insertion process has been disclosed.

CITATION LIST

Patent Literature

PTL 1: JP-A-2012-21871

SUMMARY OF INVENTION

Technical Problem

In the above related art, the allowable number of times of insertion into the lid is determined, which makes it possible to suppress generation of foreign matter and the like. However, in the above related art, no consideration is given to wear and deformation of the probe. In other words, as the probe is repeatedly inserted into the lid, the lid deteriorates due to wear and deformation, but no consideration is given to generation of foreign matter from the lid due to deterioration of the probe side.

Since the lid itself is made of an elastic member such as rubber, deterioration of the probe does not occur to a great extent by a single insertion. However, due to the need for improving a dispensing processing ability in recent years, the insertion speed of the probe tends to be larger than before, and one insertion load applied to the probe is relatively large. On the other hand, deterioration such as wear and deformation of the probe leads to deterioration of the sharpness of the probe, and in the case where the sharpness is greatly deteriorated, a problem such as generation of foreign matter occurs, regardless of the number of times of insertion into the same lid.

As a result, the probe is to be replaced in a case where the sharpness of the probe deteriorates, but until now, at the stage when foreign matter is generated, the operator notices the problem and replaces the probe. However, after foreign matter is generated, analysis results may be wasted due to generation of foreign matter, analysis may not be performed during replacement, and there is a concern that a processing efficiency is reduced.

Although it may be considered to replace the probe with a period as a reference, the operation situation of the device differs depending on a facility, it is difficult to derive a relationship between the deterioration degree of the sharpness of the probe and the period. It is uneconomical to replace a probe uniformly during a set time, regardless of the operation situation. For example, even in a case where the number of times of analysis is small, the sharpness of the probe is not deteriorated, and the probe can still be used, the probe has to be replaced.

In the technique of PTL 1, the degree of deterioration of the probes cannot be known and the above-described problem cannot be solved. The present invention has been made in view of the above problems, and an object of the present invention is to provide an automatic analyzer capable of replacing a probe according to the degree of deterioration of the probe while suppressing occurrence of dispensing abnormality and analysis result abnormality.

In addition, in particular, because the number of times of insertion of the probe is large, it is effective to know the degree of deterioration, and a blade or a hollow tube is used as a mechanism to be inserted into the lid, in addition to the probe, it is effective to know the degree of deterioration because it is a measure of replacement.

Solution to Problem

In order to achieve the above object, a representative present invention provides an automatic analyzer including an insertion mechanism that is inserted into a closed container through a lid of the container; a storage unit that stores an insertion history count corresponding to a cumulative load of the insertion mechanism caused by inserting the insertion mechanism into a plurality of the containers, and an allowable insertion history count which is an allowable value of the insertion history count; and a control unit that compares the insertion history count with the allowable insertion history count and performs control to make a notification to an operator in a case where the insertion history count reaches the allowable insertion history count.

Since the operator can know that the allowable insertion history count has been reached, the operator can replace an insertion mechanism, before the occurrence of dispensing abnormality and analysis result abnormality caused by foreign matters of the lid.

Advantageous Effects of Invention

According to the present invention, it is possible to replace the insertion mechanism while suppressing occurrence of dispensing abnormality and analysis result abnormality accompanying deterioration of an insertion mechanism.

DESCRIPTION OF EMBODIMENTS

Hereinafter, embodiments of the present invention will be described with reference to the drawings.

The "insertion history count" used in the present specification is a number corresponding to the cumulative load of the insertion mechanism caused by inserting the insertion mechanism across a plurality of lidded containers. This "insertion history count" is an index of the deterioration degree of the insertion mechanism. The insertion mechanism corresponds to a probe, a blade, a hollow tube, or the like.

Example 1

Figure 1:
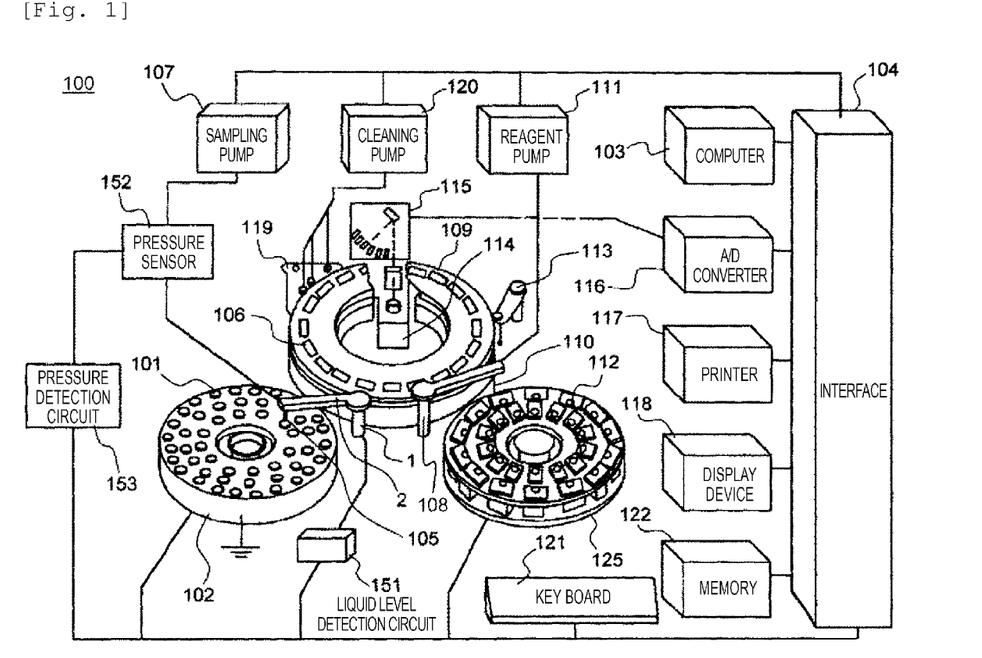
FIG. 1 is a diagram schematically showing a dispensing mechanism of an automatic analyzer according to a first embodiment of the present invention together with its peripheral configuration.

FIG. 1 is a diagram schematically showing a dispensing mechanism of an automatic analyzer according to a first embodiment of the present invention together with its peripheral configuration.

In FIG. 1, an automatic analyzer 100 according to the present embodiment includes a sample disc 102 on which a sample container 101 containing a sample 7 is placed and is rotationally driven, a reaction disc 109 on which a reaction container 106 is placed and is rotationally driven, a reagent disc 125 on which reagent bottles 112 containing reagents corresponding to a plurality of analysis items to be analyzed in the automatic analyzer are placed and is rotationally driven, a sampling mechanism 1 for dispensing the sample 7 in the sample container 101 into the reaction container 106, a reagent dispensing mechanism 108 for dispensing the reagent in the reagent bottle 112 into the reaction container 106, and a control unit (computer) 103 that controls the whole operation including each unit of the automatic analyzer 100.

The sampling mechanism 1 includes a sampling arm 2 that is vertically driven and rotationally driven, and a sampling probe 105 that is provided at the tip of the sampling arm 2, and dispenses the sample 7, by the sampling probe 105 sucking the sample 7 in the sample container 101 and dispensing it into the reaction container 106, according to the operation of a sampling syringe pump 107 provided in the automatic analyzer 100.

The reagent dispensing mechanism 108 also has the same configuration as that of the sampling mechanism 1, and dispenses the reagent, by the reagent dispensing probe 110 sucking the reagent in the reagent bottle 112 and dispensing it into the reaction container 106, according to the operation of a reagent syringe pump 111 provided in the automatic analyzer 100.

The control unit (computer) 103 controls the overall operation of the automatic analyzer 100 by exchanging signals with the respective configuration units of the automatic analyzer 100 through the interface 104, and performs an analysis process of each sample based on information and instructions relating to analysis items or the like input from input means such as a keyboard 121 and a display device 118. Further, the analysis result is displayed on the display device 118 (for example, CRT), printed out by the printer 117, or stored in a memory (for example, a hard disc) which is the storage unit 122.

Figure 2:
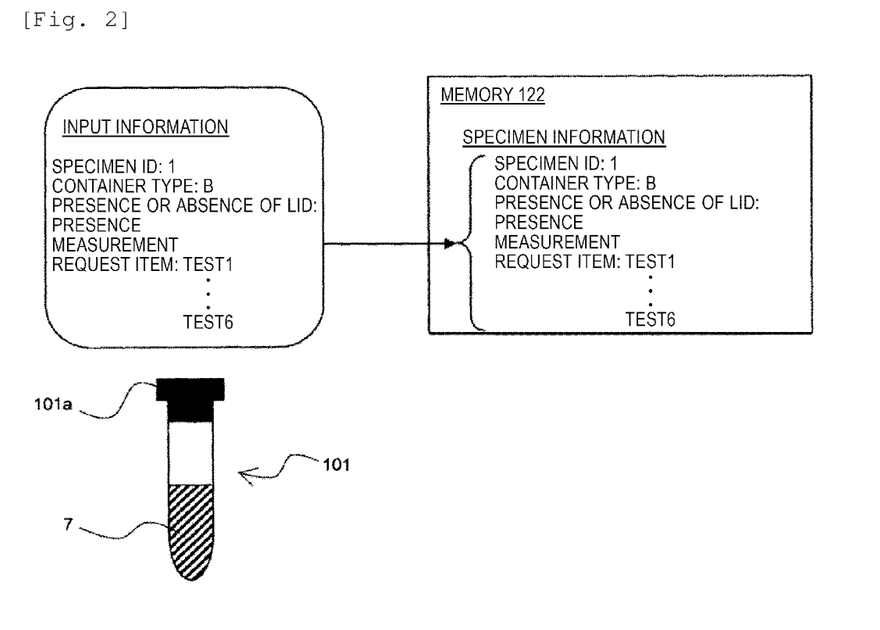
FIG. 2 is a diagram conceptually showing the states of specimen information input to a storage unit and various types of information stored therein.

FIG. 2 is a diagram conceptually showing the states of specimen information which is input to a storage unit (hereinafter, also referred to as a memory), and various types of stored information. For the sake of explanation, FIG. 2 schematically shows the sample container.

As shown in FIG. 2, the sample container 101 contains the sample 7 and is hermetically sealed by the lid 101a. The operator inputs information of the specimen in each sample container 101 to the storage unit 122 by input means such as the keyboard 121. In the present embodiment, the case of inputting the specimen ID, the container type, the presence or absence of a lid, and the measurement request item is shown. An individual identification tag (specimen ID) such as a bar code or an RFID, not shown, is provided in the sample container 101, so that the accommodated sample 7 can be identified. In the present embodiment, the sample container 101 having the following information will be described as an example.

(Input Information)
Specimen ID: 1
Container type: B
Presence or absence of lid: Presence
Measurement request items: TEST 1 to TEST 6

In the information stored in the storage unit 122, in addition to the above-described input information, a numerical value (hereinafter referred to as an insertion history count K) representing the insertion history of the probe is stored. The insertion history count is, for example, a value calculated by the following Equation (1), and $k_i$ is an increase amount of the insertion history count at the time of i-th insertion. In addition, $k_i$ is a function with the type of the lid into which the probe is inserted, the insertion speed of the probe, the temperature of the lid, the presence or absence of perforation as variables (a, b, c . . . ).

$$K=\Sigma k_i(a,b,c\ldots) \qquad (1)$$

In other words, it corresponds to quantifying the load amount applied to the probe once and digitizing the load amount. Factors affecting the load amount include the insertion speed of the probe, the temperature of the lid, and the presence or absence of perforation. In addition, there may be no such variables and only a number of times or a variable may be 1 or more. The more variables, the higher the accuracy of the load amount.

As a simple example, in the case of the same type of lid, the number of times of simply inserting the probe into the lid can be calculated as the insertion history count. Alternatively, it may not be the number of times itself, but may be a value proportional to the number of times of insertion into the lid. That is, the insertion history count is calculated based on a value proportional to the number of times of insertion into the lid.

In addition, in a case of penetrating lids of different types, the loads applied at the time of penetration of the respective lids are considered. For example, it is assumed that the types of lids are A and B, and the A lid is harder than the B lid. Since the lid is a rubber stopper, it means relative hardness. In this case, since the load on the probe in the lid A is larger than in the lid B, the load coefficient of A is made larger than that of B. For example, it is assumed that A is 1.0 and B is 0.8. In a case where probes are inserted into the lids A and B 10000 times, respectively, the insertion history count is 18000 (10000×1.0+10000×0.8). In other words, the insertion history count is calculated, based on the load coefficient corresponding to the type of lid and the number of times of insertion for each lid. If the hardness values of the lids A and B are substantially equal, the load coefficient may be both 1.0 and the sum of both the number of times of insertion may be used. The load coefficient is stored in the storage unit 122.

Further, a case is considered where the insertion speed of the probe into the lid, the temperature of the lid, and the presence or absence of perforation of the lid are important as the load amount of the probe, rather than the type of the lid. The faster the insertion speed of the probe, the greater the load on the probe. Further, as the temperature of the lid is low, it becomes hard, so the load on the probe increases as the temperature is low. Further, if there is perforation of the lid, the resistance of the lid is low. If there is no perforation, the resistance of the lid is high. Therefore, the load of the probe is large if there is no perforation. These factors may be digitized as load coefficients to determine the function of Equation (1). In other words, the storage unit 122 stores one of the type of the lid, the speed of insertion of the probe, the temperature of the lid, and the presence or absence of perforation of the lid, as a condition for inserting the probe into the sample container through the lid, as a load coefficient. The insertion history count is calculated based on the load coefficient corresponding to the above condition and the number of times of insertion under the condition. It may be a load coefficient obtained by combining the two, three, or four conditions. The more the number of combinations, the better the accuracy of the load amount, so it is preferable to have many combinations.

As a representative combination of two conditions, a combination of the type of the lid and the presence or absence of perforation of the lid is conceivable. For example, if a load coefficient without perforation of the lid A is set to 1.0, a load coefficient with perforation of the lid A is set to 0.2, a load coefficient without perforation of the lid B is set to 0.8, a load coefficient with perforation of the lid B is set to 0.1, and the number of times of insertion under each condition is 10000, the insertion history count is 21000 (10000×1.0+10000×0.2+10000×10000×0.8+10000×0.1). The condition without the perforation of a hard lid is the largest load coefficient, and the condition with the perforation of a soft lid is the smallest load coefficient. The load coefficient in the case of the presence of perforation may be zero. That is, the insertion history count is calculated based on the load coefficient by this combination and the number of times of insertion for each combination.

In addition, the memory 122 also stores the insertion history count (hereinafter, referred to as an allowable insertion history count $K_0$) in which it is necessary to replace a probe.

The allowable insertion history count $K_0$ is obtained empirically from results obtained by preliminary experiments, and is the insertion history count of a probe in which there is no substantially possibility of occurrence of dispensing abnormality and analysis result abnormality due to insertion of the sampling probe 105 into the lid 101a.

Here, the outline of the analysis process in the automatic analyzer 100 will be described.

First, the sample container 101 containing the sample 7 is transferred to the sample sucking position in accordance with the intermittent rotation of the sample disc 102, and the sampling probe 105 is lowered in the sample container 101 which is stopped at the suction position. If the tip of the sampling probe 105 comes into contact with the liquid surface of the sample 7 with the lowering operation, a detection signal is output from the liquid level detection circuit 151, and the detection signal is input to the control unit 103 through the interface 104. The control unit 103 controls to stop the lowering operation by the driving unit (not shown) of the sampling arm 2, based on the detection signal. In this state, after sucking a predetermined amount of sample in the sampling probe 105, the sampling probe 105 rises to the top dead center. In addition, during the suction operation in which the sampling probe 105 sucks a predetermined amount of the sample 7, the pressure detection circuit 153 detects pressure fluctuation in the flow path between the sampling probe 105 and the sampling syringe pump 107 using a signal from the pressure sensor 152. In a case where an abnormality is found in the pressure fluctuation in the flow path during the suction operation, it is determined that there is a high possibility that the predetermined amount of the sample is not sucked, and an alarm is added to the analysis data.

Next, the sampling arm 2 is pivotally driven in the horizontal direction, the sampling probe 105 is lowered at the position of the reaction container 106 transferred to the sample discharge position in accordance with the rotation operation of the reaction disc 109, and the sample 7 which has been held in the inside of the reaction container 106 is discharged. Thereafter, the reaction container 106 containing the sample 7 is moved to the reagent addition position in accordance with the rotation operation of the reaction disc 109, and a reagent corresponding to the analysis item is added from the reagent dispensing probe 110. With the dispensing of the sample and the reagent, the liquid level of the sample in the sample container 101 and the liquid level of the reagent in the reagent bottle 112 are detected, and the remaining amounts of the sample and the reagent are calculated based on the detection result, and stored in the storage unit 122. The mixture in the reaction container 106 to which the sample and the reagent are added is stirred by the stirrer 113. As a plurality of reaction containers cross the light flux from the light source 114 during the transfer of the reaction container row in accordance with the rotation operation of the reaction disc 109, the absorbance or light emission value of each mixture is measured (photometered) by the photometer 115 which is measuring means. A measurement signal (an absorbance signal or a light emission value signal) is input to the control unit 103 through the interface 104 through the A/D converter 116, and the concentration of the analysis item is calculated. The analysis result is printed out to the printer 117 through the interface 104 or output to the display device 118 such as a CRT as a screen, and stored in the storage unit 122 such as a hard disc.

The reaction container 106 whose photometry is ended is transported to the position of the cleaning mechanism 119 and is cleaned by supply of cleaning water into the reaction container 106 by the cleaning pump 120 and discharge of waste liquid.

As can be seen from FIG. 1, the placement of the sample container 101 on the sample disc 102 is structured to correspond to a case of placing the sample container 101 directly on the sample disc 102 or a universal placement capable of placing the sample container 101 on a test tube (not shown). In addition, three rows of container holding portions are formed so that three rows of sample containers 101 can be placed concentrically on the sample disc 102, and sample suction positions by the sampling probes 105 are set one by one in each row.

Further, the dispensing process of the sampling mechanism 1 will be described.

Figure 3:
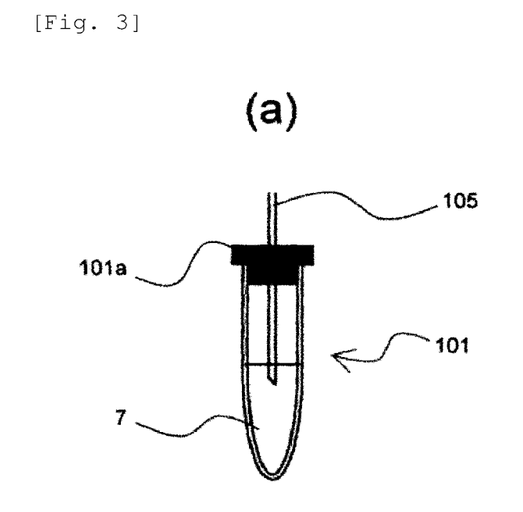
FIG. 3 is a diagram schematically showing a state of insertion of a sampling probe of a sampling mechanism 1 into a sample container.

FIG. 3 is a diagram schematically showing a state of insertion of the sampling probe 105 of the sampling mechanism 1 into a sample container 101.

As shown in FIG. 3, the sample container 101 placed on the sample disc 102 contains the sample 7 and is hermetically sealed by the lid 101a. The sampling probe 105 to be inserted into such a sample container 101 has a sharp distal end shape, and has a function of performing a cutting process for making a cut in the lid 101a and a function of being immersed in the sample 7 to perform suction. In a case of performing a cutting process on the lid 101a (including a case of being immersed in the sample 7 to perform suction), or in a case where the probe is inserted into the sample container 101 through the cut in the lid 101a which has already been opened and is immersed in the sample 7 to perform suction, the insertion history count is updated.

Figure 4:
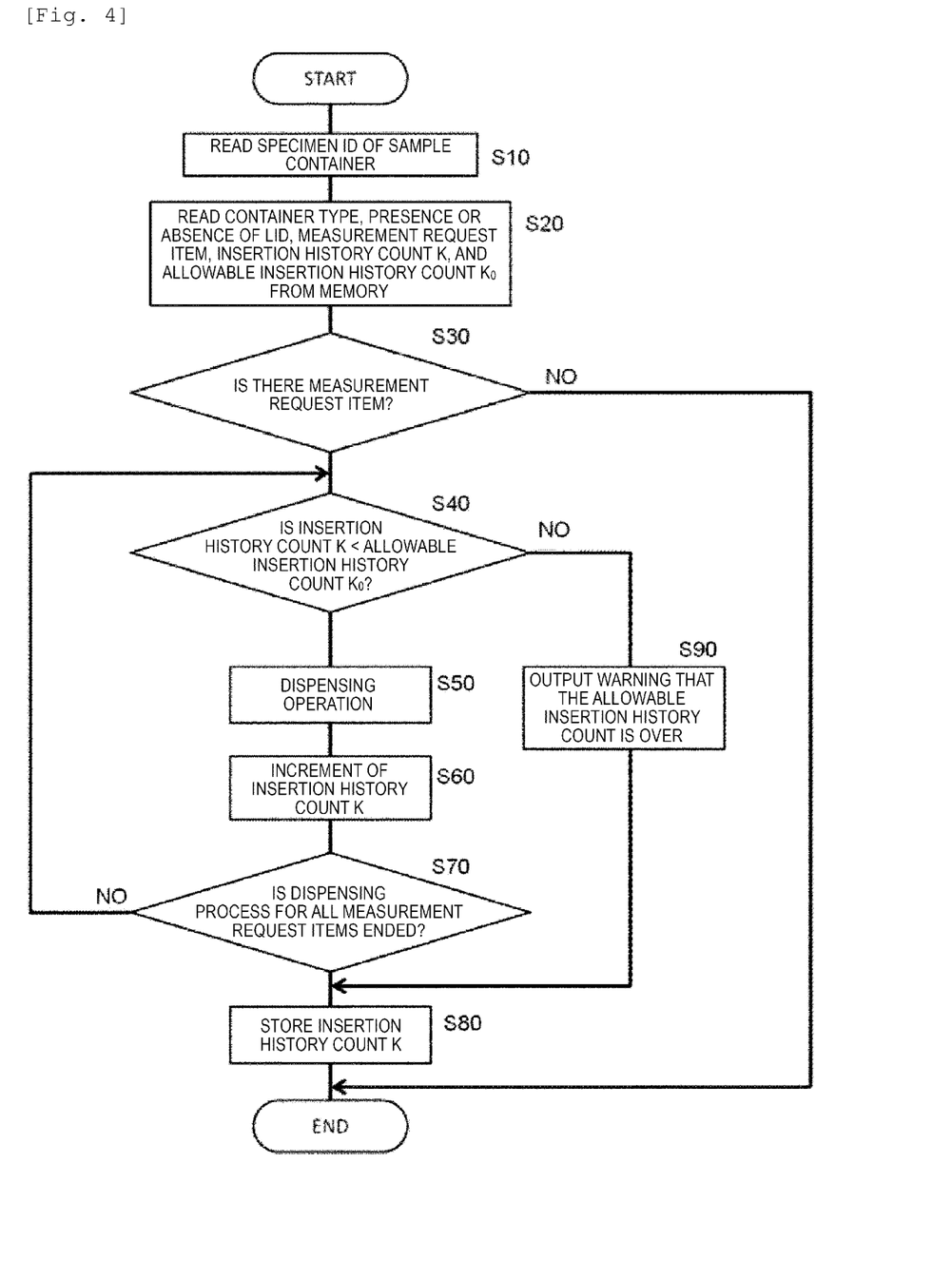
FIG. 4 is a flowchart showing details of a dispensing process.

FIG. 4 is a flowchart showing details of the dispensing process.

In the analysis process according to the present embodiment, the control unit 103 first reads the specimen ID of the sample container 101 to be dispensed (step S10). Next, information such as the container type of the sample container 101, the type of the lid, the presence or absence of the lid, and the measurement request items, the probe insertion history count K, the allowable insertion history count $K_0$, and the like are read from the storage unit 122, based on the read specimen ID (step S20). Next, it is determined whether or not there is a measurement request item (step S30). In a case where the determination result is NO, the dispensing process is ended, and the process moves to the dispensing process of the next sample container 101 to be dispensed. In a case where the determination result in step S30 is YES, the control unit 103 determines whether or not the insertion history count K is smaller than the allowable insertion history count $K_0$ (step S40), in a case where the determination result is YES, the dispensing operation (insertion of the sampling probe 105 through the lid 101a to the sample container 101, suction of the sample 7, and discharge to the reaction container 106) is performed (step S50), and thereafter the insertion history count K (K←K+$k_i$) is incremented (step S60). The insertion history count $k_i$ to be added is determined by the simple number of times, or by a load coefficient considering any condition of the type of the lid, the insertion speed of the probe, the temperature of the lid, and the presence or absence of perforation of the lid. Then, it is determined whether or not the dispensing process for all the measurement request items is ended (step S70). If the determination result is YES, the insertion history count K is stored (step S80), and the dispensing process is ended. In a case where the determination result in step S40 is NO, an alarm of a probe replacement request is output and is notified to the operator (step S90), the insertion history count K is stored (step S80), and the dispensing process is ended. Further, in a case where the determination result in step S70 is NO, the processes from steps S40 to S70 are repeated until the dispensing process for all the measurement request items is ended and the determination result in step S70 is YES. In a case where the determination result in step S40 is NO during the repetition of steps S40 to S70, the repetition is ended and an alarm of a probe replacement request is output (step S90), the insertion history count K is stored (step S80), and the dispensing process is ended.

In the dispensing process, in a case where the alarm of a probe replacement request is output (step S90) and the dispensing process is ended, the operator takes out the target sample container 101 from the sample disc 102, removes the lid 101a manually, places it again on the sample disc 102 to restart the dispensing operation. In the dispensing process in this case (in the case of handling the sample container 101 without the lid 101a), the comparison between the insertion history count K and the allowable insertion history count $K_0$ (step S40), the increment of the insertion history count K (step S60), and saving of the insertion history count K (step S80) are skipped, without being performed.

In the present embodiment configured as described above, the sampling probe 105 constitutes an insertion mechanism to be inserted into the container through the lid of the closed container, and the storage unit 122 stores the insertion history count K of the inserting mechanism to the container. This flow is repeated even in another sample container, and the insertion history count K is accumulated. Thus, almost all of the load on the probe can be accumulated after the use of the device is started.

The operation of the present embodiment configured as described above will be described.

First, as preparation for analysis processing, a sample container 101 containing a sample 7, closed with a lid 101a, is placed on the sample disc 102, and a reagent bottle 112 corresponding to a plurality of analysis items to be analyzed is placed on the reagent disc 125. In addition, specimen information (the specimen ID, the container type, the type of the lid, presence or absence of the lid, measurement request items, or the like) on each sample container 101 is input by input means such as the keyboard 121. By instructing the start of analysis processing in this state, analysis processing of the specimen by the automatic analyzer is started.

In the analysis process, first, the sample 7 accommodated in the sample container 101 is subjected to a dispensing process by the sampling probe 105 attached to the sampling arm 2 of the sampling mechanism 1, and dispensed into the reaction container 106. In the dispensing process, based on the specimen ID read from the sample container 101 to be subjected to the dispensing process, the control unit 103 first reads information such as the container type of the sample container 101, the type of the lid, the presence or absence of the lid, and the measurement request items, the insertion history count K, the allowable insertion history count $K_0$, and the like from the storage unit 122 (steps S10 and S20 in FIG. 4). In a case where there is no measurement request item, the dispensing process is ended, and the process moves to the dispensing process of the next sample container 101 to be dispensed (step S30 in FIG. 4). In a case where there is a measurement request item and the insertion history count K is smaller than the allowable insertion history count $K_0$, the dispensing operation (insertion of the sampling probe 105 into the sample container 101 through the lid 101a and suction of the sample 7) and the increment of the insertion history count K are repeatedly performed until the dispensing process for all the measurement request items is ended (steps S40 to S70 in FIG. 4). If the dispensing process for all the measurement request items is ended, the insertion history count K is updated and saved, the dispensing process is ended, and the process moves to the dispensing process of the next sample container 101 to be dispensed (step S80 in FIG. 4). In a case where the insertion history count K becomes equal to or greater than the allowable insertion history count $K_0$ during the dispensing process, an alarm of a probe replacement request is output and the operator is notified of the alarm, the insertion history count K is stored (step S90 and S80 in FIG. 4), the dispensing process is ended.

In addition, in the dispensing process, in a case where the alarm of a probe replacement request is output (step S90) and the dispensing process is ended, the operator takes out the target sample container 101 from the sample disc 102, removes the lid 101a manually, places it again on the sample disc 102, and repeats the dispensing operation until the dispensing process for all the measurement request items is ended, irrespective of the existing insertion history count. The same also applies to a case where the sample container 101 without the lid 101a is handled.

Subsequently, the reagent contained in the reagent bottle 112 is dispensed into the reaction container 106 by the reagent dispensing probe 110 of the reagent dispensing mechanism 108, and a mixture in the reaction container 106 to which the reagent is added to the sample is stirred by a stirrer 113. As a plurality of reaction containers cross the light flux from the light source 114 during the transfer of the reaction container row in accordance with the rotation operation of the reaction disc 109, the absorbance or light emission value of each mixture is measured (photometered) by the photometer 115 which is measuring means. A measurement signal (an absorbance signal or a light emission value signal) is input to the control unit 103 through the interface 104 through the A/D converter 116, and the concentration of the analysis item is calculated. That is, a concentration analysis of the analysis items of the sample 7 is performed based on the photometric result of the photometer 115. The reaction container 106 whose photometry is ended is transported to the position of the cleaning mechanism 119 and is cleaned by supply of cleaning water into the reaction container 106 by the cleaning pump 120 and discharge of waste liquid.

Effects of the present embodiment configured as described above will be described.

In the related art, an allowable insertion count N is set for each container type, and in a case where the number n of times of insertion of the probe exceeds the allowable insertion count N, the operator is notified of an alarm that the allowable insertion count is over for the container. However, in the above-mentioned related art, only the allowable insertion count is set for a certain container, and no consideration is given to occurrence of foreign matter or the like from the lid due to deterioration of the probe. Therefore, according to the related art, it is not possible to prevent occurrence of foreign matter due to deterioration of the probe and the like. For example, if the probe has an extremely bad sharpness, occurrence of foreign matter or the like may occur one or two times.

In contrast, the present embodiment is configured such that the insertion history count indicating the insertion history of the probe and the allowable insertion history count which is the threshold for issuing the probe replacement request are stored in the storage unit 122, and thus a probe replacement request can be announced at an appropriate timing by managing the cumulative load amount (damage) of the probe such as wear and deformation. That is, since an alarm based on the cumulative amount of damage on the probe is issued, it is possible to notify the probe replacement request at an appropriate timing while suppressing generation of foreign matter at the time of dispensing.

The present embodiment is configured such that in a case where the insertion history count K of the probe is equal to or greater than the allowable insertion history count $K_0$ in the dispensing process, an alarm of a probe replacement request is output and the operator is notified of the alarm and ends the dispensing process. However, it may be configured so as to temporarily stop the analysis process automatically, or it may be configured so as to be able to set them. Alternatively, it may be configured such that after the sample is sucked with a probe and the probe is withdrawn from the lid, cleaning of the outside of the probe, a foreign matter removing operation such as blowing, or a removal operation due to a partial discharge of the sample held in the probe is performed, and then the sample is dispensed into a reaction container. Further, it may be configured to execute or to be able to set them.

Example 2

Figure 5:
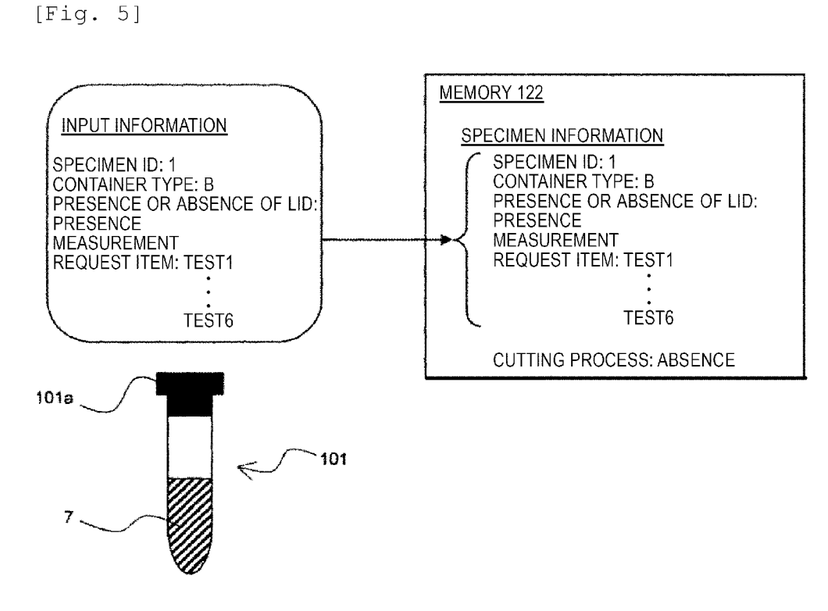
FIG. 5 is a diagram conceptually showing the states of specimen information input to a storage unit and various types of information stored therein, according to a second embodiment of the present invention.
Figure 6:
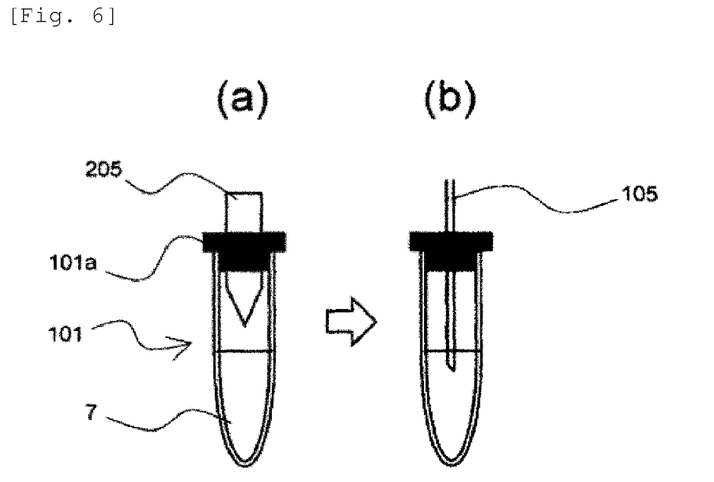
FIG. 6 is a diagram schematically showing a state of insertion of a blade and a sampling probe of a sampling mechanism into a sample container, according to a second embodiment of the present invention.
Figure 7:
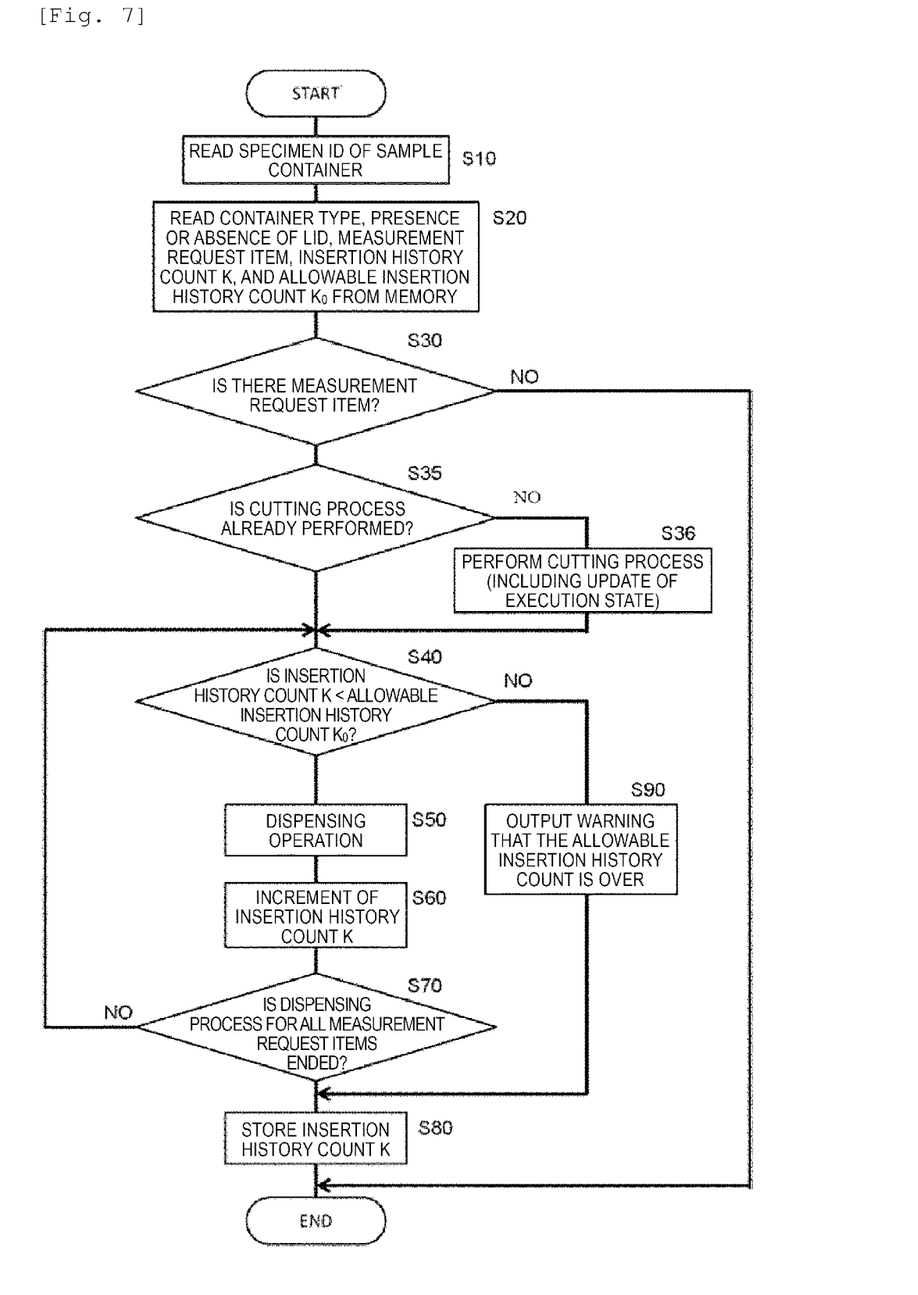
FIG. 7 is a flowchart showing details of a dispensing process according to the second embodiment of the present invention.

A second embodiment of the present invention will be described with reference to FIGS. 5 to 7. The present embodiment is configured such that in addition to the configuration shown in the first embodiment, a blade 205 for performing a cutting process on the lid 101a of the sample container 101 is further provided to insert the sampling probe 105, and the execution state (whether or not it is executed) of the cutting process and the existing insertion history count of the blade 205 into the lid 101a in the dispensing process are managed. FIG. 5 is a diagram conceptually showing the states of the specimen information input to the storage unit and the various types of information stored therein, FIG. 6 is a diagram schematically showing the state of insertion of the blade 205 and the sampling probe 105 of the sampling mechanism 1 into the sample container 101, according to the present embodiment, and FIG. 7 is a flowchart showing details of the dispensing process according to the present embodiment. In the drawings, the same members as those described in the first embodiment are denoted by the same reference numerals, and description thereof is omitted.

As shown in FIG. 5, the sample container 101 contains the sample 7 and is hermetically sealed by the lid 101a. The operator inputs information of the specimen in each sample container 101 to the storage unit 122 by input means such as the keyboard 121. In the present embodiment, the case of inputting the specimen ID, the container type, the presence or absence of a lid, and the measurement request item is shown. An individual identification tag (specimen ID) such as a bar code or an RFID, not shown, is provided in the sample container 101, so that the accommodated sample 7 can be identified. In addition to the information input by the operator, the information stored in the storage unit 122 includes the insertion history count K of each probe, the execution state (whether it is executed or not) of the cutting process, the allowable insertion history count $K_0$ of each probe, or the like. The insertion history count is a value calculated by Equation (1), and $k_i$ is an increase amount of the insertion history count at the time of i-th insertion.

Further, K is a function with the type of the lid into which the probe is inserted, the insertion speed of the probe, the temperature of the lid, the presence or absence of perforation, and the like as variables (a, b, c . . . ).

In addition, the storage unit 122 also stores the insertion history count (hereinafter, referred to as an allowable insertion history count $K_0$) in which it is necessary to replace a probe. The insertion history count $K_0$ is obtained empirically from results obtained by preliminary experiments, and is the insertion history count of a probe in which there is no substantially possibility of occurrence of dispensing abnormality and analysis result abnormality due to insertion of the sampling probe 105 into the lid 101a. Further, like the probe, the insertion history count for the blade is also stored in the storage unit.

As shown in FIG. 6, the sample container 101 placed on the sample disc 102 contains the sample 7 and is hermetically sealed by the lid 101. A blade 205 to be inserted into the sample container 101 has a sharp tip shape and has a function of performing a cutting process to cut the lid 101a (see FIG. 6(a)). The sampling probe 105 is inserted into the sample container 101 through the cut in the lid 101a subjected to the cutting process and is immersed in the sample 7 to perform suction (see FIG. 6(b)). In the case where the sampling probe 105 is inserted into the sample container 101 through the cut in the lid 101a and is immersed in the sample 7 to perform suction, the insertion history count described above is updated.

As shown in FIG. 7, in the analysis process according to the present embodiment, the computer 103 first reads the specimen ID of the sample container 101 to be dispensed (step S10). Next, based on the read specimen ID, specimen information such as the container type of the sample container 101, the type of the lid, the presence or absence of the lid, the measurement request items, and the implementation state of the cutting process (presence or absence of perforation of the lid), the insertion history count K, the allowable insertion history count $K_0$, and the like are read from the storage unit 122 (step S220). Next, it is determined whether or not there is a measurement request item (step S30). In a case where the determination result is NO, the dispensing process is ended, and the process moves to the dispensing process of the next sample container 101 to be dispensed. In a case where the determination result in step S30 is YES, it is determined whether or not the cutting process has been performed (step S35). Subsequently, in a case where the determination result is YES, it is determined whether or not the existing insertion history count K is smaller than the allowable insertion history count $K_0$ (Step S40). In a case where the determination result in step S35 is NO, a cutting process (including update of the information on the execution state in the specimen information) is performed (step S36). Subsequently, it is determined whether or not the insertion history count K is smaller than the allowable insertion history count $K_0$ (Step S40). In a case where the determination result in step S40 is YES, the dispensing operation (insertion of the sampling probe 105 through the lid 101a to the sample container 101, suction of the sample 7, and discharging to the reaction container 106) is performed (step S50), and thereafter the existing insertion history count K ($K \leftarrow K+k_i$) is incremented (step S60). The insertion history count $k_i$ to be added is determined by the simple number of times, or by a load coefficient considering any condition of the type of the lid, the insertion speed of the probe, the temperature of the lid, and the presence or absence of perforation of the lid. Then, it is determined whether or not the dispensing process for all the measurement request items is ended (step S70). If the determination result is YES, the existing insertion history count K is stored (step S80), and the dispensing process is ended. In a case where the determination result in step S40 is NO, an alarm of a probe replacement request is output and is notified to the operator (step S90), the insertion history count K is stored (step S80), and the dispensing process is ended. Further, in a case where the determination result in step S70 is NO, the processes from steps S40 to S70 are repeated until the dispensing process for all the measurement request items is ended and the determination result in step S70 is YES. In a case where the determination result in step S40 is NO during the repetition of steps S40 to S70, the repetition is ended and an alarm of a probe replacement request is output (step S90), the insertion history count K is stored (step S80), and the dispensing process is ended.

In the dispensing process, in a case where the alarm of a probe replacement request is output (step S90) and the dispensing process is ended, the operator takes out the target sample container 101 from the sample disc 102, removes the lid 101a manually, places it again on the sample disc 102 to restart the dispensing operation. In the dispensing process in this case (in the case of handling the sample container 101 without the lid 101a), confirmation of the execution state of the cutting process (step S35), the comparison between the insertion history count K and the allowable insertion history count $K_0$ (step S40), the increment of the insertion history count K (step S60), and saving of the insertion history count K (step S80) are skipped, without being performed.

Further, if attention is paid to the blade, the storage unit also stores the insertion history count and the allowable insertion history count for the blade. However, in the case where there is perforation of the lid, since the blade is not practically inserted into the container, the loads to be considered are the simple number of times, or load coefficients based on the type of the lid, the insertion speed of the blade, and the temperature of the lid. By executing the cutting process in step S36, a load satisfying the processing condition is calculated, and the insertion history count is updated. The insertion history count $k_i$ to be added is determined by the simple number of times, or by a load coefficient considering any condition of the type of the lid, the insertion speed of the probe, and the temperature of the lid. In the same manner as in the case of the probe, the control unit compares the accumulated insertion history count with the allowable insertion history count, and in a case where the insertion history count K becomes equal to or greater than the allowable insertion history count $K_0$ during the dispensing process, an alarm of a blade replacement request is output and the operator is notified of the alarm, the insertion history count K is stored.

In the present embodiment configured as described above, the sampling probe 105 constitutes an insertion mechanism to be inserted into the container through the lid of the closed container, and the storage unit 122 stores the insertion history count of the inserting mechanism to the container. This flow is repeated even in another sample container, and the insertion history count K of the sample probe is accumulated. Thus, almost all of the load on the probe can be accumulated after the use of the device is started. Further, this flow is repeated even in another sample container, and the insertion history count K of the blade is accumulated. Thus, almost all of the load on the blade can be accumulated after the use of the device is started.

The operation of the present embodiment configured as described above will be described.

First, as preparation for analysis processing, a sample container 101 containing a sample 7, closed with a lid 101a, is placed on the sample disc 102, and a reagent bottle 112 corresponding to a plurality of analysis items to be analyzed is placed on the reagent disc 125. In addition, specimen information (the specimen ID, the container type, the type of the lid, presence or absence of the lid, measurement request items, or the like) on each sample container 101 is input by input means such as the keyboard 121. By instructing the start of analysis processing in this state, analysis processing of the specimen by the automatic analyzer is started.

In the analysis process, first, the sample 7 accommodated in the sample container 101 is subjected to a dispensing process by the blade 205 and the sampling probe 105 attached to the sampling arm 2 of the sampling mechanism 1, and dispensed into the reaction container 106. In the dispensing process, based on the specimen ID read from the sample container 101 to be subjected to the dispensing process, the control unit 103 first reads information such as the container type of the sample container 101, the type of the lid, the presence or absence of the lid, the measurement request items, and the implementation state of the cutting process, the insertion history count K, the allowable insertion history count $K_0$, and the like from the storage unit 122 (steps S10 and S20 in FIG. 7). In a case where there is no measurement request item, the dispensing process is ended, and the process moves to the dispensing process of the next sample container 101 to be dispensed (step S30 in FIG. 4). If there is a measurement request item, a cutting process (including update of specimen information) is performed in a case where the cutting process is not performed, and the cutting process is not performed in a case where the cutting process has been performed (steps S35 and S36 in FIG. 7). Subsequently, in a case where the insertion history count K is smaller than the allowable insertion history count $K_0$, the dispensing operation (insertion of the sampling probe 105 into the sample container 101 through the lid 101a and suction of the sample 7) and the increment of the insertion history count K are repeatedly performed until the dispensing process for all the measurement request items is ended (steps S40 to S70 in FIG. 7). If the dispensing process for all the measurement request items is ended, the insertion history count K is updated and saved, the dispensing process is ended, and the process moves to the dispensing process of the next sample container 101 to be dispensed (step S80 in FIG. 7). In a case where the insertion history count K becomes equal to or greater than the allowable insertion history count $K_0$ during the dispensing process, an alarm of a probe replacement request is output and the operator is notified of the alarm, the insertion history count K is stored (step S90 and S80 in FIG. 7), the dispensing process is ended.

In addition, in the dispensing process, in a case where the alarm that the allowable insertion history count is over is output (step S90) and the dispensing process is ended, the operator takes out the target sample container 101 from the sample disc 102, removes the lid 101a manually, places it again on the sample disc 102, and repeats the dispensing operation until the dispensing process for all the measurement request items is ended, irrespective of the insertion history count K. The same also applies to a case where the sample container 101 without the lid 101a is handled.

Further, as described above about the blade, the storage unit also stores the insertion history count and the allowable insertion history count for the blade. By executing the cutting process in step S36, a load satisfying the processing condition is calculated, and the insertion history count is updated. In the same manner as in the case of the probe, the control unit compares the accumulated insertion history count with the allowable insertion history count, and in a case where the insertion history count K becomes equal to or greater than the allowable insertion history count $K_0$ during the dispensing process, an alarm of a blade replacement request is output and the operator is notified of the alarm, the insertion history count K is stored. In the present embodiment, the case where the insertion history count is calculated for both the probe and the blade, but it may be applied only to the blade.

Subsequently, the reagent contained in the reagent bottle 112 is dispensed into the reaction container 106 by the reagent dispensing probe 110 of the reagent dispensing mechanism 108, the sample and a mixture in the reaction container 106 to which the reagent is added is stirred by a stirrer 113. As a plurality of reaction containers cross the light flux from the light source 114 during the transfer of the reaction container row in accordance with the rotation operation of the reaction disc 109, the absorbance or light emission value of each mixture is measured (photometered) by the photometer 115 which is measuring means. A measurement signal (an absorbance signal or a light emission value signal) is input to the control unit 103 through the interface 104 through the A/D converter 116, and the concentration of the analysis item is calculated. The reaction container 106 whose photometry is ended is transported to the position of the cleaning mechanism 119 and is cleaned by supply of cleaning water into the reaction container 106 by the cleaning pump 120 and discharge of waste liquid.

In the present embodiment configured as described above, the same effects as those of the first embodiment can be obtained.

Further, since the implementation state of the cutting process on the lid 101a of the sample container 101, that is, a state indicating whether it is implemented or not is stored in the storage unit 122, it is possible to suppress the occurrence of foreign matter and mixture into the sample accompanying the dispensing of the sample 7, and suppress occurrence of dispensing abnormality and analysis result abnormality. That is, since the state of insertion of the blade 205 into the lid 101a (implementation state of the cutting process) is stored and managed in the storage unit 122, it is possible to prevent duplication of the cutting process on the lid 101a, it is possible to suppress occurrence of foreign matters and mixing into the sample accompanying the dispensing of the sample 7, and it is possible to suppress occurrence of dispensing abnormality and analysis result abnormality.

The present embodiment is configured such that in a case where the insertion history count K of the sample container 101 to be dispensed is equal to or greater than the allowable insertion history count $K_0$ in the dispensing process, an alarm that the allowable insertion history count is over is output and the operator is notified of the alarm and ends the dispensing process. However, it may be configured so as to temporarily stop the analysis process automatically, or it may be configured so as to be able to set them. Alternatively, it may be configured such that after the sample is sucked with a probe and the probe is withdrawn from the lid, cleaning of the outside of the probe, a foreign matter removing operation such as blowing, or a removal operation due to a partial discharge of the sample held in the probe is performed, and then the sample is dispensed into a reaction container. Further, it may be configured to execute or to be able to set them. This applies not only to probes but also to blades.

Example 3

Figure 8:
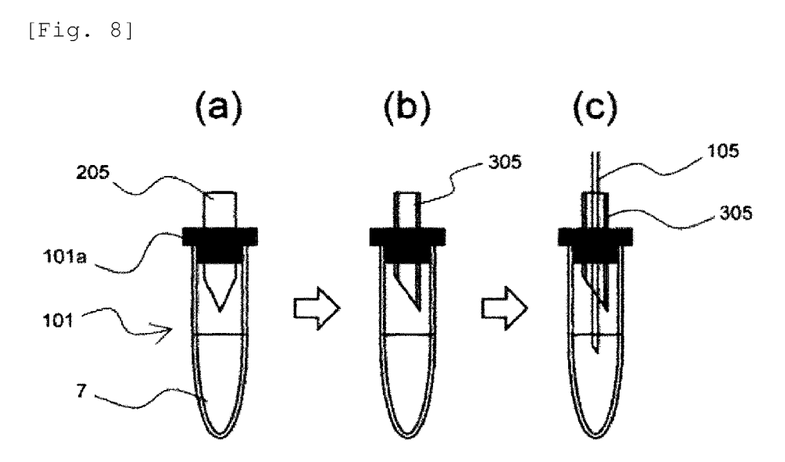
FIG. 8 is a diagram schematically showing a state of insertion of a blade, a hollow tube and a sampling probe of a sampling mechanism into a sample container, according to a third embodiment of the present invention.
Figure 9:
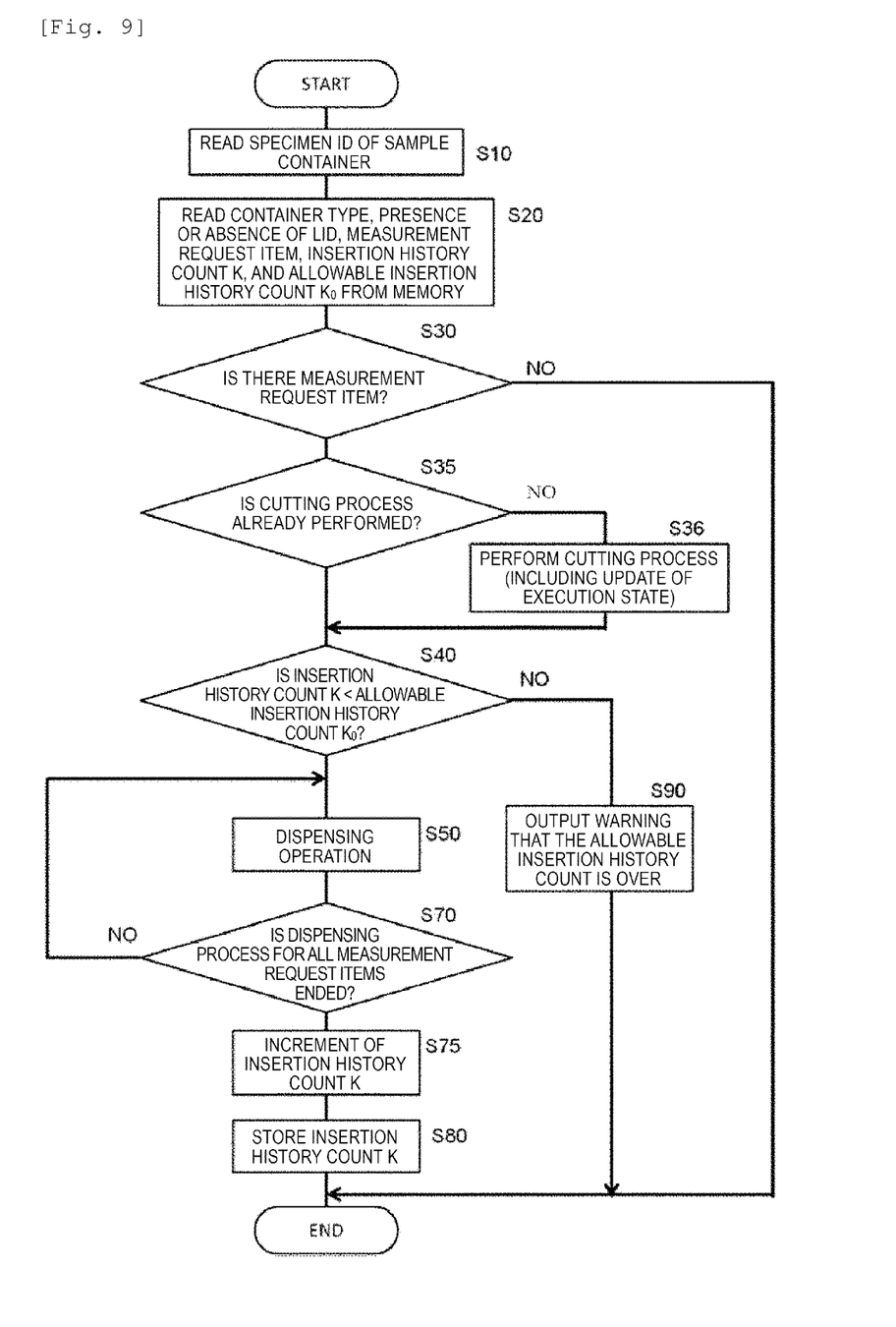
FIG. 9 is a flowchart showing details of a dispensing process according to the third embodiment of the present invention.

A third embodiment of the present invention will be described with reference to FIGS. 8 and 9. The present embodiment is configured such that in addition to the configuration shown in the second embodiment, a hollow tube 305 for passing the sampling probe 105 is further provided, and the existing insertion history count of the hollow tube 305 into the lid 101a in the dispensing process is managed. As in the second embodiment, the insertion history count of the blade may be managed. FIG. 8 is a diagram schematically showing a state of insertion of the blade 205, the hollow tube 305, and the sampling probe 105 of the sampling mechanism 1 into the sample container 101 according to the present embodiment, and FIG. 9 is a flowchart showing details of the dispensing process according to the present embodiment. In the drawings, the same members as those described in the first embodiment are denoted by the same reference numerals, and description thereof is omitted.

As shown in FIG. 8, the sample container 101 placed on the sample disc 109 contains the sample 7 and is hermetically sealed by the lid 101a. The blade 205 inserted into such a sample container 101 has a sharp distal end shape, and has a function of performing a cutting process for making a cut in the lid 101a (see FIG. 8(a)). The hollow tube 305 is inserted into the sample container 101 through the cut in the lid 101a subjected to the cutting process by the blade 205 (see FIG. 8(b)), and the sampling probe 105 passes through the inside of the hollow tube 305 and is inserted into the sample container 101 and is immersed in the sample 7 to perform suction (see FIG. 8(c)). In the present embodiment, the case where the hollow tube 305 is inserted into the sample container 101 through the cut in the lid 101a corresponds to the case of counting the insertion history count described above.

As shown in FIG. 9, in the analysis process according to the present embodiment, the control unit 103 first reads the specimen ID of the sample container 101 to be dispensed (step S10). Next, based on the read specimen ID, specimen information such as the container type of the sample container 101, the presence or absence of the lid, the measurement request items, and the implementation state of the cutting process, the insertion history count K of the hollow tube 305, the allowable insertion history count $K_0$, and the like are read from the storage unit 122 (step S320). Next, it is determined whether or not there is a measurement request item (step S30). In a case where the determination result is NO, the dispensing process is ended, and the process moves to the dispensing process of the next sample container 101 to be dispensed. In a case where the determination result in step S30 is YES, it is determined whether or not the cutting process has been performed (step S35). Subsequently, in a case where the determination result is YES, it is determined whether or not the insertion history count K of the hollow tube 305 is smaller than the allowable insertion history count $K_0$ (Step S40). In a case where the determination result in step S35 is NO, a cutting process (including update of the information on the execution state in the specimen information) is performed (step S36). Subsequently, it is determined whether or not the insertion history count K of the hollow tube 305 is smaller than the allowable insertion history count $K_0$ (Step S40). In a case where the determination result in step S40 is YES, the dispensing operations (insertion of the hollow tube 305 into the sample container 101 through the lid 101a, insertion of the sampling probe 105 into the sample container 101 through the hollow tube 305, suction of the sample 7, and discharge to the reaction container 106) are performed (step S50). Thereafter, it is determined whether or not the dispensing process for all the measurement request items is ended (step S70). If the determination result is YES, the hollow tube 305 is extracted from the lid 101a, the increment of the insertion history count K ($K \leftarrow K+k_i$) of the hollow tube 305 is performed (step S70), the insertion history count K is stored (step S80), and the dispensing process is ended. The insertion history count $k_i$ of the hollow tube to be added is determined by the simple number of times, or by a load coefficient considering any condition of the type of the lid, the insertion speed of the hollow tube, and the temperature of the lid. In a case where the determination result in step S40 is NO, an alarm of a hollow tube replacement request is output and is notified to the operator (step S90), and the dispensing process is ended. Further, in a case where the determination result in step S70 is NO, the processes of steps S50 and S70 are repeated until the dispensing process for all the measurement request items is ended and the determination result in step S70 is YES, while maintaining the inserted state of the hollow tube 305 into the lid 101a. In a case where the determination result in step S40 is NO during the repetition of steps S40 to S70, the repetition is ended and an alarm of the hollow tube replacement request is output (step S90), and the dispensing process is ended.

In the dispensing process, in a case where the alarm of a hollow tube replacement request is output (step S90) and the dispensing process is ended, the operator takes out the target sample container 101 from the sample disc 102, removes the lid 101a manually, places it again on the sample disc 102 to restart the dispensing operation. In the dispensing process in this case (in the case of handling the sample container 101 without the lid 101a), confirmation of the execution state of the cutting process (step S35), the comparison between the insertion history count K of the hollow tube and the allowable insertion history count $K_0$ (step S40), the increment of the insertion history count K (step S75), and saving of the insertion history count K (step S80) are skipped, without being performed.

In the present embodiment configured as described above, the sampling probe 105 constitutes an insertion mechanism to be inserted into the container through the lid of the closed container, and the storage unit 122 stores the insertion history count of the inserting mechanism to the container. This flow is repeated even in another sample container, and the insertion history count K of the hollow tube is accumulated. Thus, almost all of the load on the hollow tube can be accumulated after the use of the device is started.

The operation of the present embodiment configured as described above will be described.

First, as preparation for analysis processing, a sample container 101 containing a sample 7, closed with a lid 101a, is placed on the sample disc 102, and a reagent bottle 112 corresponding to a plurality of analysis items to be analyzed is placed on the reagent disc 125. In addition, specimen information (the specimen ID, the container type, the type of the lid, presence or absence of the lid, measurement request items, or the like) on each sample container 101 is input by input means such as the keyboard 121. By instructing the start of analysis processing in this state, analysis processing of the specimen by the automatic analyzer is started.

In the analysis process, first, the sample 7 accommodated in the sample container 101 is subjected to a dispensing process by the blade 205 and the sampling probe 105 attached to the sampling arm 2 of the sampling mechanism 1, and dispensed into the reaction container 106. In the dispensing process, based on the specimen ID read from the sample container 101 to be subjected to the dispensing process, the control unit 103 first reads information such as the container type of the sample container 101, the type of the lid, the presence or absence of the lid, the measurement request items, and the implementation state of the cutting process, the insertion history count K of the hollow tube 305, the allowable insertion history count $K_0$, and the like from the storage unit 122 (steps S10 and S320 in FIG. 9). In a case where there is no measurement request item, the dispensing process is ended, and the process moves to the dispensing process of the next sample container 101 to be dispensed (step S30 in FIG. 9). If there is a measurement request item, a cutting process (including update of specimen information) is performed in a case where the cutting process is not performed, and the cutting process is not performed in a case where the cutting process has been performed (steps S35 and S36 in FIG. 9). Subsequently, in a case where the insertion history count K of the hollow tube is smaller than the allowable insertion history count $K_0$, the dispensing operations (insertion of the hollow tube 305 into the sample container 101 through the lid 101a, insertion of the sampling probe 105 into the sample container 101 through the hollow tube 305, and suction of the sample 7) are repeatedly performed until the dispensing process for all the measurement request items is ended (steps S50 and S70 in FIG. 9). If the dispensing process for all the measurement request items is ended, the insertion history count K of the hollow tube is incremented and the insertion history count K is updated and saved, the dispensing process is ended, and the process moves to the dispensing process of the next sample container 101 to be dispensed (steps S75 and S80 in FIG. 9).

In addition, in the dispensing process, in a case where the alarm of a probe replacement request is output (step S90) and the dispensing process is ended, the lid operator takes out the target sample container 101 from the sample disc 102, removes the lid 101a manually, places it again on the sample disc 102, and repeats the dispensing operation until the dispensing process for all the measurement request items is ended, irrespective of the existing insertion history count n. The same also applies to a case where the sample container 101 without the lid 101a is handled.

Subsequently, the reagent contained in the reagent bottle 112 is dispensed into the reaction container 106 by the reagent dispensing probe 105 of the reagent dispensing mechanism 108, the sample and a mixture in the reaction container 106 to which the reagent is added is stirred by a stirrer 113. As a plurality of reaction containers cross the light flux from the light source 114 during the transfer of the reaction container row in accordance with the rotation operation of the reaction disc 109, the absorbance or light emission value of each mixture is measured (photometered) by the photometer 115 which is measuring means. A measurement signal (an absorbance signal or a light emission value signal) is input to the computer 103 through the interface 104 through the A/D converter 116, and the concentration of the analysis item is calculated. The reaction container 106 whose photometry is ended is transported to the position of the cleaning mechanism 119 and is cleaned by supply of cleaning water into the reaction container 106 by the cleaning pump 120 and discharge of waste liquid.

In the present embodiment configured as described above, the same effects as those of the first and second embodiments can be obtained.

Further, since the insertion history count of the hollow tube 305 into the lid 101a of the sample container 101 is stored in the storage unit 122, it is possible to suppress the occurrence of foreign matter and mixing into the sample accompanying the dispensing of the sample 7, and suppress occurrence of dispensing abnormality and analysis result abnormality. That is, since the insertion history count of the hollow tube 305 into the lid 101a is stored and managed in the storage unit 122, and the allowable insertion history count $K_0$ is set so that insertion exceeding that number cannot be performed, it is possible to suppress occurrence of foreign matters and mixing into the sample accompanying the dispensing of the sample 7, and it is possible to suppress occurrence of dispensing abnormality and analysis result abnormality.

The present embodiment is configured such that in a case where the insertion history count K of the sample container 101 to be dispensed is equal to or greater than the allowable insertion history count $K_0$ in the dispensing process, an alarm of hollow tube replacement request is output and the operator is notified of the alarm and ends the dispensing process. However, it may be configured so as to temporarily stop the analysis process automatically, or it may be configured so as to be able to set them. Alternatively, it may be configured such that after the sample is sucked with a probe and the probe is withdrawn from the lid, cleaning of the outside of the probe, a foreign matter removing operation such as blowing, or a removal operation due to a partial discharge of the sample held in the probe is performed, and then the sample is dispensed into a reaction container. Further, it may be configured to execute or to be able to set them.

In the embodiment of the present invention, the case where the operator inputs the type of the container and the type of the lid has been described as an example, but the present invention is not limited to this, and may adopt a configuration that includes a container type determination unit or a lid type determination unit that determines the type of the container or the type of the lid from the container image captured with a camera or the like, a configuration that performs determination from a bar code or an RFID, and a configuration that performs determination from a passage time of the lid at the time of container movement using a reflection type sensor, and the like. It may be configured to include a cutting state determination unit that determines the execution state of the cutting process from the image of the lid 101a obtained by capturing the execution state of the cut process of the lid 101a with a camera or the like. Further, the specimen ID may be managed by a HOST computer in a higher hierarchy than the automatic analyzer 100. In this case, it is possible to share the existing number of times of dispense among a plurality of automatic analyzers managed by the HOST computer. Furthermore, the storage period of the existing number of times of dispense may be arbitrarily set, and it is possible to prevent a reset operation error of the existing number of times of dispense.

Furthermore, in the case of a configuration without a determination unit that determines the presence or absence of the lid 101a, with respect to a target sample to which an alarm of a replacement request of an insertion mechanism (a probe, a blade, or a hollow tube) is output, it may be configured such that if the operator does not input information indicating that the lid 101a is removed, from the input means such as the keyboard 121, the analysis of the target sample is not resumed. In this case, it is possible to reduce the probability of occurrence of human error such as forgetting to take out the lid 101a.

In the embodiment of the present invention, the case where in a case where the insertion history count K is larger than the allowable insertion history count $K_0$, the operator is notified of the alarm of the insertion mechanism (the probe, the blade, or the hollow tube) replacement request, and the dispensing operation is not performed has been described as an example, but apart from this, in a case where the difference between the insertion history count K and the allowable insertion history count $K_0$ becomes smaller than a certain threshold $\Delta K$, an alarm of an insertion mechanism replacement notice may be notified, and a dispensing operation may be performed. A certain threshold $\Delta K$ in this case may be a fixed value, may be set by an operator, or may be automatically set from a statistical value such as a dispense frequency of a day. Alternatively, a plurality of thresholds $\Delta K$ may be set, and different alarms may be notified respectively.

In order to suppress the increase amount of the insertion history count K by one perforation, for example, the perforation ability may be changed by lowering the dispensing processing ability, or a mechanism for heating the lid portion may be provided in the device. In this case, it is desirable to provide a heating unit for heating the lid portion before the insertion mechanism passes through the lid of the container.

Resetting of the insertion history count K after the replacement of the insertion mechanism may be input by the operator from input means such as a keyboard 121 or the like. At this time, in order to prevent human errors such as forgetting to replace the insertion mechanism, if an operation (detailed later) of confirming whether the insertion mechanism is replaced is not performed after resetting the insertion history count K, the dispensing operation may not be performed. That is, the insertion history count can be reset, and in a case where the reset is performed and the control unit does not receive the replacement information of the insertion mechanism, it is desirable that the control unit does not perform the inserting operation of the replaced insertion mechanism. The replacement information can be input manually or automatically.

In particular, it can be automatically determined whether or not the probe is replaced. For example, the determination is performed by observing the probe using a camera, measuring a change in pressure at the time of suction/discharge, checking the stop position using a jig or the like, or the like. Alternatively, the dispensing operation may be performed with a special lidded container for checking the state of the probe. The lid can be made of such a material that foreign matters do not occur at the time of dispensing with a new probe, but with a probe having an insertion history count sufficiently smaller than the allowable insertion history count, foreign matters are generated at the time of dispensing. Confirmation of the presence or absence of foreign matters at this time may be performed using a reagent whose color is changed by contact with foreign matters, or by measuring the change in color with absorbance.

Although the load coefficient is stored in advance in the storage unit, the load coefficient can be changed. Since the operation environment varies depending on facilities, it may be better to change the load coefficient after operating the device. Accordingly, it is desirable to provide a display device in which the setting of the load coefficient can be changed.

Further, in a case of changing the load coefficient or the like, there are cases where it is desired to check the insertion history count when the insertion mechanism is replaced. This is because more accurate load coefficient can be set again with reference to the past insertion history count. Therefore, it is desirable that a display device that displays the insertion history count when the insertion mechanism is replaced is provided, the storage unit stores the insertion history count when the insertion mechanism is replaced, and the display device displays a list of the insertion history count at the time of replacement. In addition, it is desirable to display the type of the lid and the number of times of insertion for each lid on the list display side by side with the insertion history count.

In addition, the insertion history count is a numerical value indicating the degree of deterioration, which is the cumulative load of the insertion mechanism, but the insertion history count may be calculated by taking factors other than the number of times of insertion and factors other than the load coefficient into account. Therefore, the insertion history count may not be a value itself proportional to the number of times of insertion, or may be based on the number of times of insertion. In addition, the insertion history count may not be the integrated value itself of the load coefficient corresponding to the type of the lid and the number of times of insertion for each lid, or may be based on the integral value.

Further, in the present embodiment, the sample disc 102 type has been described as an example, but the present invention can also be applied to a so-called rack type case. In the case of the rack type, the sample container 101 is transported by the rack.

It should be noted that the present invention is not limited to the above-described embodiments, and various modifications are included without departing from the concept of the invention.

REFERENCE SIGNS LIST

1 SAMPLING MECHANISM
2 SAMPLING ARM
7 SAMPLE
100 AUTOMATIC ANALYZER
101 SAMPLE CONTAINER
101A LID
102 SAMPLE DISC
103 CONTROL UNIT (COMPUTER)
104 INTERFACE
105 SAMPLING PROBE
106 REACTION CONTAINER
107 SAMPLE SYRINGE PUMP
108 REAGENT DISPENSING MECHANISM
109 REACTION DISC
110 REAGENT DISPENSING PROBE
111 REAGENT SYRINGE PUMP
112 REAGENT BOTTLE
113 STIRRER
114 LIGHT SOURCE
115 PHOTOMETER
116 A/D CONVERTER
117 PRINTER
118 DISPLAY DEVICE
119 CLEANING MECHANISM
120 CLEANING PUMP
121 KEYBOARD
122 STORAGE UNIT (MEMORY)
125 REAGENT DISC
151 LIQUID LEVEL DETECTION CIRCUIT
152 PRESSURE SENSOR
153 PRESSURE DETECTION CIRCUIT
205 BLADE
305 HOLLOW TUBE

The invention claimed is:

1. An automatic analyzer comprising:
an insertion mechanism that is configured to be inserted into a container through a lid of the container;
a storage device configured to store a plurality of load coefficients corresponding to a plurality of different types of lids and the plurality of load coefficients correspond to combinations of the respective type of lid and a presence or absence of perforation of the respective type of lid, to store an insertion history count corresponding to a cumulative load of the insertion mechanism caused by inserting the insertion mechanism through one or more of the different types of lids, and to store an allowable insertion history count; and
a computer programmed to control the insertion mechanism,
wherein the computer is further programmed to:
compare the insertion history count with the allowable insertion history count,
in a case where the insertion history count reaches the allowable insertion history count, output a notification to an operator,
in a case where the insertion history count does not reach the allowable insertion history count, update the insertion history count after the insertion mechanism is inserted into the container through the lid of the container based on the respective load coefficient corresponding to the type of the lid of the container and the presence or absence of perforation of the lid of the container,
wherein the insertion mechanism is a sample probe, a blade, or a hollow tube through which a sampling probe is inserted.

2. The automatic analyzer according to claim 1,
wherein the insertion history count is proportional to a number of times of insertion of the insertion mechanism.

3. The automatic analyzer according to claim 1,
wherein the computer is further programmed to update the insertion history count after the insertion mechanism is inserted into the container through the lid of the container based on the respective load coefficient corresponding to the type of the lid of the container, the presence or absence of perforation of the of lid of the container, an insertion speed of the insertion mechanism into the lid of the container, and a temperature of the lid of the container.

4. The automatic analyzer according to claim 1, wherein the computer is further programmed to:
change a setting of one or more of the load coefficients.

5. The automatic analyzer according to claim 1,
wherein the computer is further programmed to:
reset the insertion history count, and
when the reset is performed and replacement information of the insertion mechanism is not received, operation of the replaced insertion mechanism is not performed.

6. The automatic analyzer according to claim 1,
wherein the insertion mechanism is the sample probe configured to suck an object contained in the container, and
wherein the notification is an alarm of a replacement request of the sample probe.

7. The automatic analyzer according to claim 6,
wherein the computer is programmed to automatically determine that the sample probe is replaced.

8. The automatic analyzer according to claim 1,
wherein the insertion mechanism is the blade configured to make a cut in the lid and perforate the lid, and
wherein the notification is an alarm of a replacement request of the blade.

9. The automatic analyzer according to claim 1, further comprising:
a sample probe configured to suck an object contained in the closed container; and
a blade configured to make a cut in the lid and perforate the lid,
wherein the insertion mechanism is the hollow tube to be inserted into the container through a perforation in the lid formed by insertion of a blade,
wherein the computer is further programmed to control the sample probe to be inserted into the container through a hollow portion of the hollow tube, and suck the object, and
wherein the notification is an alarm of a replacement request of the hollow tube.

10. The automatic analyzer according to claim 1, further comprising:
a display device,
wherein the computer is further programmed to display a list of the insertion history count at a time of replacement of the insertion mechanism on the display device.

11. The automatic analyzer according to claim 1,
wherein the container is a sample container that contains a sample,
wherein the automatic analyzer further comprises
a reaction disc on which a reaction container containing a mixed solution of the sample and the reagent is placed; and
a photometer to measure absorbance or light emission of the mixed solution contained in the reaction container, and
wherein a concentration analysis of an analysis item of the sample is performed based on a photometric result of the photometer.

* * * * *